United States Patent
Olson et al.

(10) Patent No.: US 6,599,696 B2
(45) Date of Patent: Jul. 29, 2003

(54) EFFECTS OF MATERIALS AND SURFACE COATINGS ON ENCRUSTATION AND BIOFILM FORMATION

(75) Inventors: Merle Edwin Olson, Calgary (CA); Howard Ceri, Calgary (CA)

(73) Assignee: University Technologies International, Inc. (CA)

( * ) Notice: Subject to any disclaimer, the term of this patent is extended or adjusted under 35 U.S.C. 154(b) by 0 days.

(21) Appl. No.: 10/139,586

(22) Filed: May 2, 2002

(65) Prior Publication Data
US 2003/0068667 A1 Apr. 10, 2003

Related U.S. Application Data

(63) Continuation-in-part of application No. 09/835,562, filed on Apr. 17, 2001.
(60) Provisional application No. 60/198,083, filed on Apr. 17, 2000.

(51) Int. Cl.[7] .............................. C12Q 1/00; C12Q 1/02
(52) U.S. Cl. ................................ 435/4; 435/29; 435/34
(58) Field of Search ................................. 435/4, 29, 34

(56) References Cited

U.S. PATENT DOCUMENTS

| 2,956,931 A | 10/1960 | Goldberg |
| 3,455,788 A | 7/1969 | Curry et al. |
| 3,691,988 A | 9/1972 | Clarke |

(List continued on next page.)

FOREIGN PATENT DOCUMENTS

| CA | 1075571 | 4/1980 |
| DE | 18 12 419 | 6/1970 |
| EP | 0 709 678 A1 | 5/1996 |
| FR | 1.221.896 | 6/1960 |
| FR | 2 548 685 | 1/1985 |
| FR | 2 739 448 | 4/1997 |
| GB | 1245035 | 9/1971 |
| GB | 1 522 128 | 8/1978 |
| JP | 90 43229 | 2/1997 |
| WO | WO 83/03677 | 10/1983 |
| WO | WO 94/10838 | 5/1994 |
| WO | WO 95/27039 | 10/1995 |
| WO | WO 97/33972 | 9/1997 |

OTHER PUBLICATIONS

Becton Dickinson Labware, "Innovative Products for Cell Science Research," 41 pages.

Bower, et al., "Influences on the antimicrobial activity of surface–adsorbed nisin," *Journal of Industrial Microbiology*, vol. 15, pp. 227–233 (1995).

Costerton, et al., "Microbial Biofilms," *Annual Reviews Microbial*, vol. 49, pp. 711–743 (1995).

Costerton, et al., "Mechanism of Electrical Enhancement of Efficacy of Antibiotics in Killing Biofilm Bacteria," *Antimicrobial Agents and Chemotherapy*, vol. 38, No. 12, pp. 2803–2804, (Dec. 1994).

(List continued on next page.)

Primary Examiner—Louise N. Leary
(74) Attorney, Agent, or Firm—Burns, Doane, Swecker & Mathis, L.L.P.

(57) ABSTRACT

A method for testing the performance of surface coatings on the formation of biofilm and encrustation on materials. The method includes, providing a plurality of material retaining sites, providing the material retaining sites with a material, wherein the material models a surface likely to be involved in biofilm formation and encrustation deposit. The method further includes the steps of providing a liquid growth medium, wherein the liquid growth medium includes at least one microorganism, the liquid growth medium arranged to cover at least a portion of the material, and incubating microorganism and encrustation on the material retaining sites in the presence of the liquid growth medium.

39 Claims, 3 Drawing Sheets

U.S. PATENT DOCUMENTS

| | | | |
|---|---|---|---|
| 3,745,091 A | 7/1973 | McCormick | |
| 4,115,200 A | 9/1978 | Anderson | |
| 4,432,642 A | 2/1984 | Tolles | |
| 4,483,925 A | 11/1984 | Noack | |
| 5,017,342 A | 5/1991 | Haberzettl et al. | |
| 5,160,378 A | 11/1992 | Tuunanen et al. | |
| 5,217,493 A | 6/1993 | Raad et al. | |
| 5,312,813 A | 5/1994 | Costerton et al. | |
| 5,326,533 A | 7/1994 | Lee et al. | |
| 5,349,874 A | 9/1994 | Schapira et al. | |
| 5,462,644 A | 10/1995 | Woodson | |
| 5,605,836 A | 2/1997 | Chen et al. | |
| 5,861,306 A | 1/1999 | Pugh et al. | |
| 5,928,889 A | 7/1999 | Bakich et al. | |
| 5,981,272 A | 11/1999 | Chang | |
| 6,051,423 A | 4/2000 | Ceri et al. | |
| 6,306,646 B1 | 10/2001 | Saad et al. | |
| 6,326,190 B1 | 12/2001 | Ceri et al. | |
| 6,410,256 B1 * | 6/2002 | Ceri et al. | 435/29 |

OTHER PUBLICATIONS

Darouiche, et al., "Vancomycin Penetration into Biofilm Covering Infected Prostheses and Effect on Bacteria," *The Journal of Infectious Diseases*, vol. 170, pp. 720–723 (1994).

Evans, et al., "Susceptibility of bacterial biofilms to tobramycin: role of specific growth rate and phase in the division cycle," *Journal of Antimicrobial Chemotherapy*, vol. 25, pp. 585–591 (1990).

Gjaltema, et al., "Heterogeneity of Biofilms in Rotating Annular Reactors: Occurance, Structure, and Consequences," *Biotechnology and Bioengineering*, vol. 44, pp. 194–204 (1994).

Hussain, et al., "Radiochemical assay to measure the biofilm produced by coagulase–negative staphylococci on solid surfaces and its use to quantitate the effects of various antibacterial compounds on the formation of the biofilm," *J. Med. Microbial*, vol. 37, pp. 62–69 (1992).

Ichimiya, et al., "The Influence of Azithromycin on the Biofilm Formation of *Psuedomonas aeruginosa* in vitro," *Chemotherapy*, vol. 42, pp. 186–191 (1996).

Ichimiya, et al., "In–vitro effects of antimicrobial agents on *Pseudomonas aeruginosa* biofilm formation," *Journal of Antimicrobial Chemotherapy*, vol. 34, pp. 331–341 (1994).

Johnston, et al., "Disinfection tests with intact biofilms: combined use of the Modified Robbins Device with impedance detection," *Journal of Microbiological Methods*, vol. 21, pp. 15–26 (1995).

Miyake, et al., "Simple Method for Measuring the Antibiotic Concentration Required to Kill Adherent Bacteria," *Chemotherapy*, vol. 38, pp. 286–290 (1992).

Morek, et al., "Comparative evaluation of fleroxacin, ampicillin, trimethoprimsulfamethozazole, and gentamicin as treatment of catheter–associated urinary tract infection in a rabbit model," *International Journal of Antimicrobial Agents*, vol. 4, pp. S21–S27 (1994).

Nunc, "Weleome to Nunc," *Nunc Inter Med*, 48 pages. (Oct. 1990).

Oie, et al., "Efficacy of disinfectants against biofilms cells of methicillin–resistant *Staphylococcus aureus*," *Microbios*, vol. 85, pp. 223–225 (1996).

Olson, et al., "Evaluation of strategies for central venous catheter replacement," *Critical Care Medicine*, vol. 22, No. 6, pp. 797–804 (1992).

Olson, et al., "Amdinocillan Treatment of Catheter–Associated Bacteriuria in Rabbits," *The Journal of Infectious Diseases*, vol. 159, pp. 1065–1072 (Jun. 1989).

Patel, et al., "Susceptibilty of Biofilms of Streptococcus sanguis to chlorhexidine gluconate and cetylpyridinium chloride," *Oral Microbiology and Immunology*, vol. 11, 2 pages (1996).

Prosser, "Method of Evaluating Effects of Antiobiotics on Bacterial Biofilm," *Antimicrobial Agents and Chemotherapy*, vol. 31, No. 10, pp. 1502–1506 (1987).

Richards, et al., "An assay of Staphylococcus epidermidis biofilm responses to therapeutic agents," *The International Journal of Artificial Organs*, vol. 15, No. 11, pp. 777–787 (1993).

Richards, et al., "An assay to measure antibiotic efficacy against Staphylococus epidermidis Biofilms on Implant Surfaces," *ASAIO Journal*, pp. M570–M571 (1994).

Shigeta, et al., "Permeation of Antimicrobial Agents through *Pseudomonas aeruginosa* Biofilms: A Simple Method," *Chemotherapy*, vol. 43, pp. 340–345 (1997).

Zimmerli, et al., "Microbiological tests to predict treatment outcome in experimental device–related infections due to *Staphylococcus aureus*," *Journal of Antimicrobial Chemotherapy*, vol. 33, pp. 959–967 (1994).

McCoy, et al., "Observations of fouling biofilm formation", Canadian Journal of Microbiology, vol. 27, Issue 9, pp. 910–917 (Sep. 1981).

Morck, et al., "Therapeutic Efficacy of Fleroxacin for Eliminating Catheter–Associated Urinary Tract Infection in a Rabbit Model", The American Journal of Medicine, vol. 94 (suppl. 3A), pp. 3A–23S–3A30S (Mar. 22, 1993).

* cited by examiner

EFFECTS OF MATERIALS AND SURFACE COATINGS ON ENCRUSTATION AND BIOFILM FORMATION

CROSS REFERENCE TO RELATED APPLICATIONS

This application is a continuation-in-part of U.S. patent application Ser. No. 09/835,562, filed Apr. 17, 2001, pending, which claims priority to U.S. Provisional Patent Application No. 60/198,083, filed Apr. 17, 2000, which are incorporated herein by reference in their entirety.

FIELD OF THE INVENTION

The present invention relates to methods and devices for testing the effects of materials and surface coatings on encrustation and biofilm formation. More particularly, the present invention relates to methods and devices for testing the effects of various antimicrobial coatings on encrustation and biofilm formation on implantable medical devices.

DESCRIPTION OF THE RELATED ART

Extensive study into the growth properties of microorganisms in recent years has shown that microorganisms form complex layers that adhere to surfaces. These complex forms of microorganisms are known as biofilms, or sessile microorganisms. Biofilms may cause problems in a variety of areas including the bodies of humans and animals, food processing, health care facilities and many other industries.

It is now known widely that microorganisms in the form of biofilms are more resistant to antimicrobial reagents than planktonic microorganisms. Yet traditional testing of antimicrobial reagents is performed utilizing planktonic microorganisms. Thus, the microbial inhibitory concentration of a reagent may be underestimated, with the result that the wrong antimicrobial reagent or wrong amount of antimicrobial reagent may be used for the treatment of microbial infection.

One type of device for monitoring biofilm buildup is described in the Canadian Journal of Microbiology (1981), Volume 27, pages 910–927, in which McCoy et al. describes the use of a so-called Robins device. The Robins device includes a tube through which water in a recycling circuit can flow. The tube has a plurality of ports within the tube wall, each port being provided with a removable stud, the stud having a biofoulable surface and being capable of being retained within the port in a fixed relationship with respect to the tube so that the biofoulable surface forms part of the internal surface of the tube. Each of the studs may be removed from the ports after a desired time interval and the surfaces analyzed for the growth of microorganisms. Alternatively, any surface growth may be removed and studied independent of the stud. The number of microorganism can be estimated for instance by physical or chemical means, e.g. by detection of bacterial ATP or by further culturing the microorganisms and analyzing the products.

Referring now to U.S. Pat. No. 5,349,874, Schapira, et al. there is shown another device for biofilm growth. Bacterial growth is determined in a water carrying conduit by providing a plurality of removable studs disposed within the conduit, or in a second conduit parallel to the first. The studs may be removed for analysis of biofilm growth on the studs. Such devices that utilize removable studs in a single conduit result in rather lengthy processing times and do not provide for rapid response times for testing of several different antimicrobial reagents.

In still another device which is described in *Simple Method for Measuring the Antibiotic Concentration Required to Kill Adherent Bacteria*, Miyake et al., Chemotherapy 1992; 38, 286–290, staphylococcus aureus cells adhered to the bottom of a 96 well plastic tissue culture plate were treated with serially diluted antibiotic solutions, viability of the cells were judged by their growth after a further 24 hours incubation. This method has the disadvantage of inconsistent colonization of sessile bacteria and settling of planktonic bacteria.

In addition to studying the formation of biofilms, there is great interest in the study of the formation of encrustation on implantable medical devices. Encrustation can be described as the formation of a foreign body on an implanted medical device. Examples of such encrustation are, calcium deposits, salt deposits, other mineral deposits, or the formation of thrombus or similar biological events. Each of the devices described above utilizes pins or similar protrusions to test the formation of biofilms thereon, a shortcoming of such a system is that they only provide an approximation of encrustation and biofilm formation. Thus, there is a need for a testing device that is configured to test various surface coatings on the formation of encrustation and biofilms on various medical devices or portions of medical devices.

It would be desirable to provide an apparatus and method for testing the effects of materials, such as surface coatings, on biofilm growth and encrustation formation and deposition. In addition, it would be desirable to provide an apparatus and method for testing the effects of materials on biofilm growth which provides rapid response times and the ability to test multiple materials or antimicrobial reagents or coatings at once.

SUMMARY OF THE INVENTION

In one aspect of the invention, there is provided a method for testing the performance of surface coatings on the formation of biofilm and encrustation on materials. The method includes, providing a plurality of material retaining sites, providing the material retaining sites with a material, wherein the material models a surface likely to be involved in biofilm formation and encrustation deposit. The method further includes the steps of providing a liquid growth medium, wherein the liquid growth medium includes at least one microorganism, the liquid growth medium arranged to cover at least a portion of the material, and incubating microorganism and encrustation on the material retaining sites in the presence of the liquid growth medium.

In another aspect of the invention, there is provided a method for testing the effect of materials and surface coatings on the formation of biofilms and encrustation in a controlled environment. The method including the steps of providing a plurality of biofilm and encrustation adherent sites, coating the biofilm adherent sites with a material which acts as a model for a surface likely to be involved in biofilm and encrustation formation, and providing a liquid growth medium arranged to flow across the biofilm and encrustation adherent sites. The method further includes agitating the liquid growth medium, growing microorganisms on the biofilm and encrustation adherent sites; and measuring biofilm formation growth and encrustation deposition on the material.

BRIEF DESCRIPTION OF THE DRAWINGS

There will now be described preferred embodiments of the invention with reference to the drawings, by way of illustration, in which like numerals denote like elements and in which.

DESCRIPTION OF THE EXEMPLARY PREFERRED EMBODIMENTS

The present invention relates to methods and devices for testing the effects of materials and surface coatings on encrustation formation and biofilm formation. The apparatus includes a lid and a vessel, wherein the lid may be configured to accept various materials for testing biofilm formation and encrustation formation. For example, the lid may contain a plurality of projections onto which materials may be directly coated thereon or disposed. In a preferred embodiment, the material may be fixedly attached to the lid and/or projections utilizing a bio-compatible adhesive or other method of attachment. The vessel is adapted to receive the lid in a fluid tight communication and to retain a liquid growth medium therein.

After a material has been disposed upon the projections, the material is suspended within the vessel containing the liquid growth medium. The material is allowed to incubate for a period of time in which biofilm and/or encrustation forms upon the material. During incubation, biofilm/encrustation formation may be promoted by providing a means for causing the liquid growth medium to flow across the material. After biofilm/encrustation formation, the lid is removed from the vessel. It shall be understood, that multiple vessel lids may be prepared, wherein the lids are then disposed onto different vessels, wherein the different vessels contain different growth mediums, or where the materials disposed on the projections have been prepared in a different manner. For example, it may be desirable to test a plurality of coatings and their effects on the formation of biofilm/encrustation formation on a medical device, in this case, a plurality of lids may be prepared wherein each lid contains a number of materials that have been prepared with different antimicrobial coatings.

Figure 1:
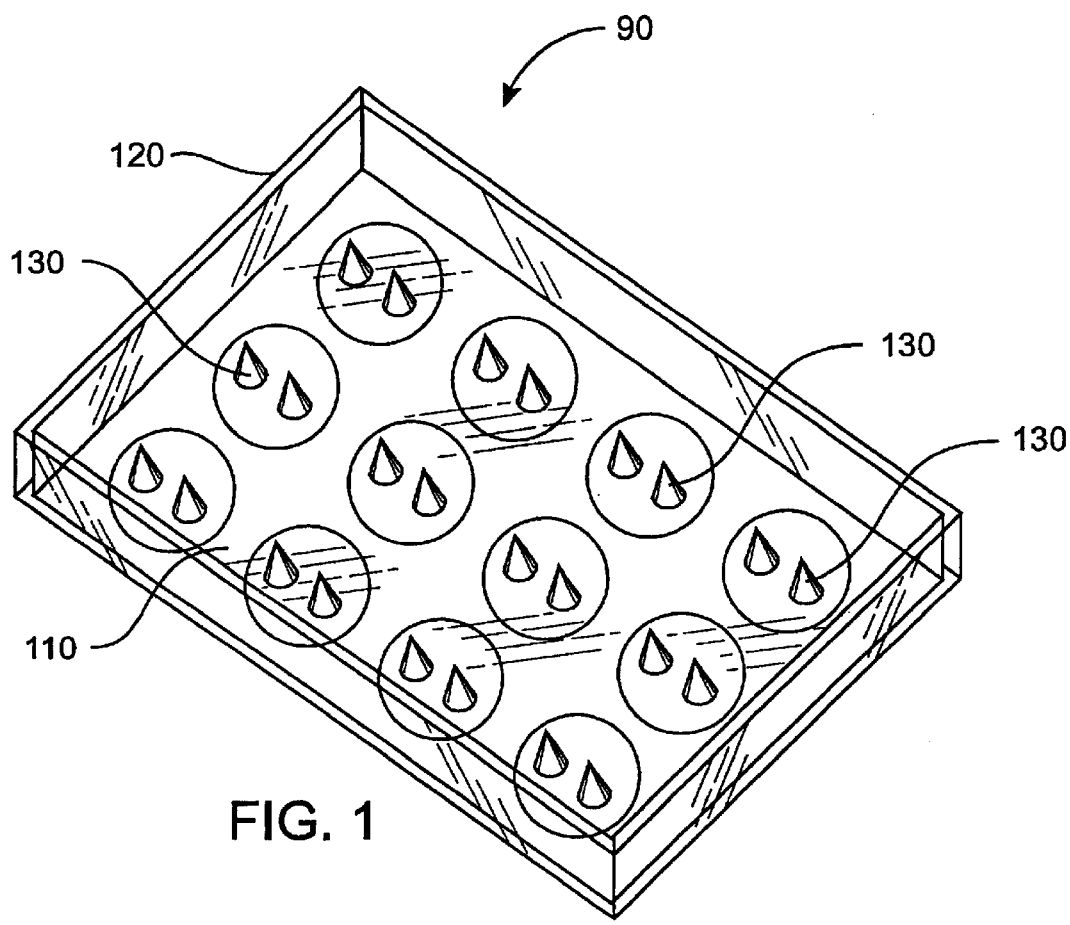
FIG. 1 is an isometric view of an exemplary embodiment the lid in accordance with the present invention.

Referring now to the FIG. 1, there is shown a perspective view of a lid 90 of a biofilm growing apparatus of the present invention. As shown in FIG. 1, the lid 90 includes a plate 100 having a first surface 110, a second surface 111 (not shown), sides 120, and a plurality of projections 130 extending from the first surface 110.

Figure 2:
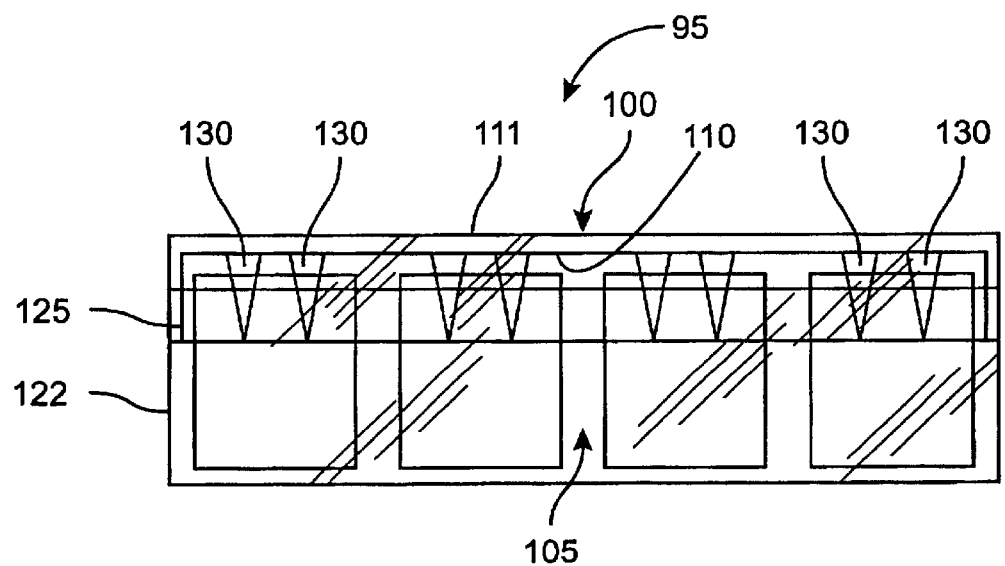
FIG. 2 is a side view of an exemplary embodiment of the vessel and lid in accordance with the present invention.

The lid 90 may be constructed of any bio-compatible material such as stainless steel, titanium, polystyrene, urethane, or low density polyethylene (LDPE). The sides 120 extend from the plate 100 and are adapted to be received by a vessel 105, as shown in FIG. 2, to form an assembly 95 having a fluid tight seal between the lid 90 and the vessel 105.

Referring now to FIG. 1, there is shown a bottom perspective view of the lid 90. The projections 130 extend from the first surface 110 of the plate 100 and have a general conical geometry. Although shown as having general conical geometry, the projections 130 may be formed having any appropriate geometry, for example, hollow cylindrical shape, solid cylindrical or square shape or any similar geometries. The projections 130 may be formed in a number of different geometrical patterns. For example, the lid 90 may be formed having 5 rows wherein each row contains 10 projections. In one embodiment, there will generally be two projections per well accommodating one sample. In a preferred embodiment the lid 90 is formed in at least three rows including at least eight projections per row.

The projections 130 are preferably unitarily formed with the plate 100 of the lid 90. Alternatively, the projections 130 may be formed by fixedly attaching an end of the projection 130 to the first surface 110 of the plate 100. Still further, the projections 130 may be formed by forming a plurality of apertures (not shown) through the first and second surfaces of plate 100 and disposing the projections 130 therethrough and affixing the projections 130 to the plate 100 with a suitable bio-compatible glue, sonic-welding, or other bio-compatible process. It is further contemplated that the projections may be made of the same material as the lid or of different materials. Still further, it is contemplated that the all of the projections may be constructed of different materials as well. The projections are arranged on the first surface 110 of the lid 90 whereby two projections are arranged such that when the lid 90 is placed upon the vessel 105 two projections 130 are disposed within each well respectively. The projections are approximately between 1 cm and 3 cm in length and about 2 millimeters wide at a widest point.

Figure 3:
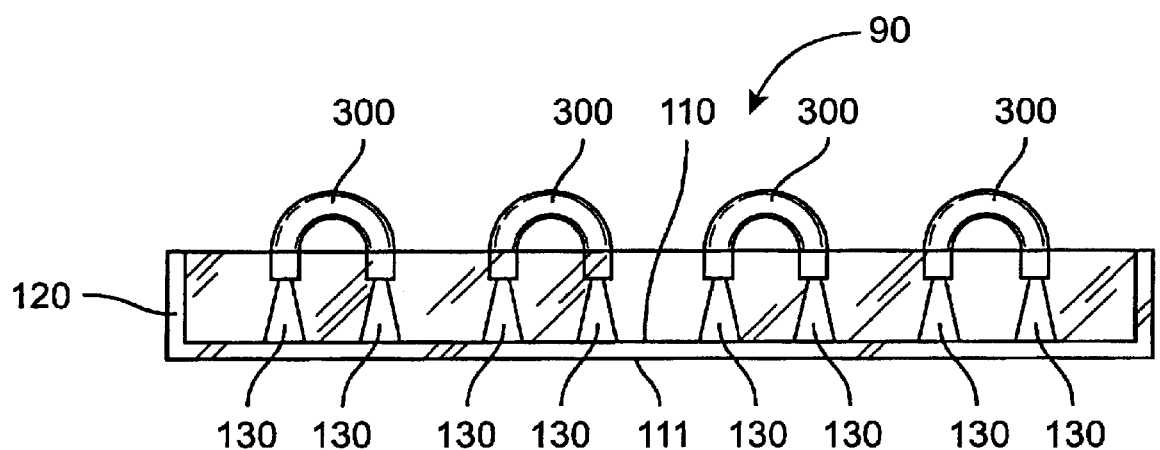
FIG. 3 is a side view of the lid of the present invention showing a biofilm growing and encrustation depositing material disposed between the projections.
Figure 4:
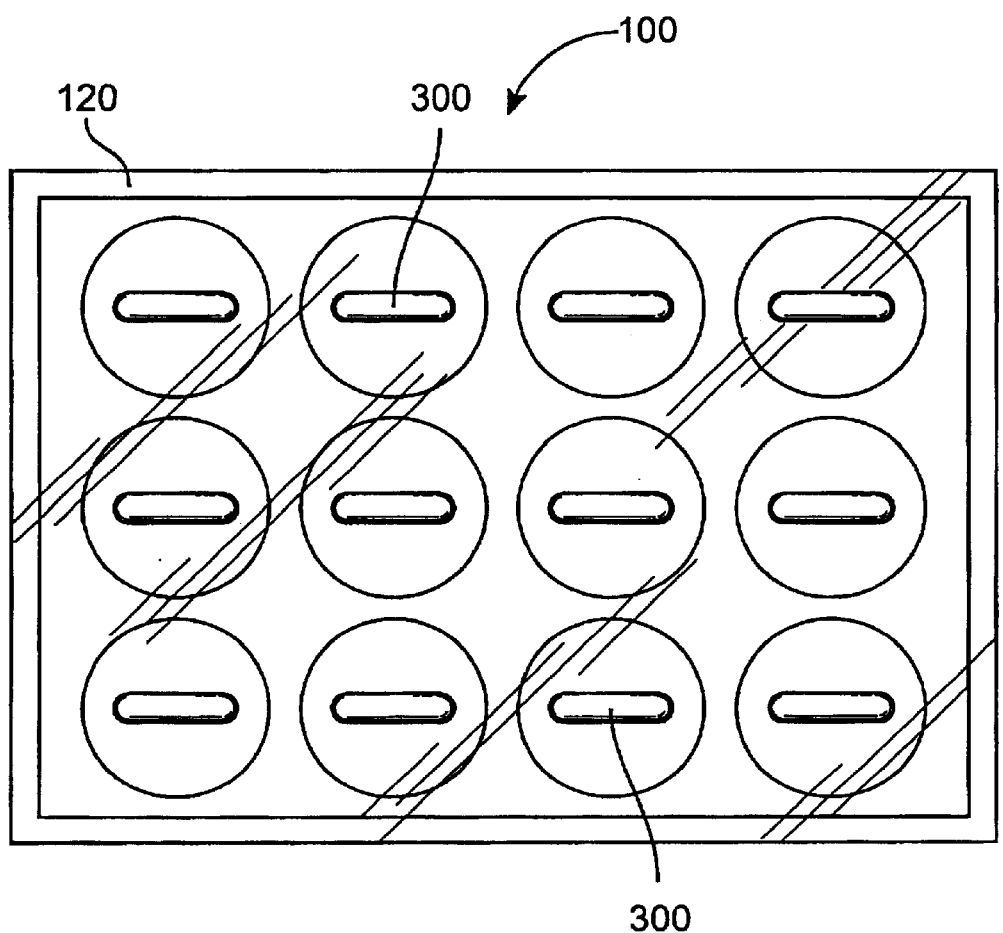
FIG. 4 is a bottom view of an exemplary embodiment of the lid in accordance with the present invention showing a biofilm growing and encrustation depositing material disposed between the projections.

Referring now to FIGS. 3 and 4, there is shown the lid 90 of the present invention having a material 300 disposed upon and between the projections 130. Referring now to FIG. 3, there is shown a side view of the lid 90 including the projections 130 wherein the material 300 is disposed between the projections 130. The material 300 may be tubing, such as a catheter that would be utilized in a medical procedure, or the material may be a portion of an implantable medical device such as a stent or similar device that may be designed for prolonged exposure within a mammalian body. The material 300 may be prepared by cutting it into small sections having a length of about 3.5 cm. One end of the material 300 is placed onto one projection 130 and the other end of the material is placed onto another adjacent projection 130, whereby the material forms and arch between the first projection and a second projection as shown in FIG. 3.

An advantage of the arrangement as shown in FIGS. 3 and 4 is that the various materials 300 being tested for the formation of biofilms and encrustation formation are tested in a manner that resembles how they would be used in vitro. Furthermore, by placing a material 300 on the projections 130 in this manner, the cut ends 301 of the material 300 are not in contact with the liquid growth medium disposed within the wells of the vessel 105. It was found that it is undesirable to expose the cut ends of the material to the liquid growth medium disposed in the vessel 105 because the cut ends of the material may not be coated with the coating to be tested, thus the test will not provide accurate results. It was also determined, that the liquid growth medium would 'wick' into the inner, un-coated surface of the material if the cut ends were in contact with the liquid growth medium. Thus, as a result it was found to be difficult to determine the formation of the biofilm/encrustation on the coated portion because of the large un-coated surface in contact with the liquid growth medium. Therefore, in a preferred embodiment, the cut ends or un-coated surfaces of the material to be tested are disposed within the assembly 95 so that they are not in contact with the liquid growth medium.

The lid 90 of the present invention allows for various materials to be simultaneously tested or removed from a vessel containing a liquid growth medium. As a result, minimal handling is required during the process. Using any of the prior art systems described above requires that each individual pin be inserted and removed, therefore it is difficult to control the overall exposure time of each of the pins in the experiment. For example, it may be desirable to test the formation of biofilm on a plurality of pins, in order to do so, each of the pins (i.e., each data point) would have to be removed and handled separately. A shortcoming of having to remove each pin separately is that this leads to inconsistent data because some pins remain in contact with the liquid growth medium longer than others, therefore the biofilm/encrustation formed using these systems is not consistent from pin to pin. The lid 90 of the present invention allows the exposure time/growth time of the biofilm to be carefully monitored and controlled by removing the entire lid 90 from the vessel 105 wherein all of the projections and biofilm growing material 300 are affixed to the lid 90. Therefore, the process of removing the lid correlates to removing all of the projections/material from the liquid growth media simultaneously. Thus, the lid 90 promotes uniform biofilm/encrustation formation on each of the projections/materials because all of the projections can be removed from the vessel in a single action. The production of uniform biofilm/encrustation formation is important to ensure that test results are uniform and accurate. Still further, the apparatus and methods of the present invention allows for high throughput of biofilm/encrustation formation because a large number of biofilm/encrustation formation sites may be prepared at once.

The material 300 may include any material in which it is desirable to test the formation of biofilm growth thereupon. For example, it may be desirable to test the growth of biofilms on an aluminum surface, thus the material 300 would include small sections of aluminum tubing disposed upon the projections 130. The material 300 may be retained on the pins by a friction fit. If necessary, a bio-compatible adhesive or other means may be utilized to retain the material 300 upon the projections 130.

It shall be understood that although specific references have been made to specific materials regarding the material 300 this shall not be considered limiting in any manner. The material 300 may include any material in which it is desirable to study the growth of biofilm thereon. The material 300 may include aluminum, steel, copper, stainless steel, titanium, silicon, urethane, or similar materials. As shown in FIG. 3, the material 300 may be disposed over more than one projection 130 whereby when the lid 90 is placed on the vessel 105, the ends of the material 300 do not contact a liquid growth medium disposed within the wells 125 of the vessel 105. Furthermore, although the material 300 has been shown as being disposed over the projections forming a u-shape, it is contemplated that the material 300 may be disposed upon the projections in a different manner than that described and shown. It is also contemplated that the material 300 may further include at least one coating in which it is desirable to test the formation of biofilm/encrustation on the coating. For example, the material 300 may be a catheter which is prepared in the manner described above, in which the catheter has been coated with a coating in which it is desirable to determine the formation of biofilm/encrustation on the coating. Such coatings may comprise aluminum, stainless steel, silver, copper, hydroxypatite, silicon, latex, urethane, PVC, and ceramic, steel, gold, titanium, polyethylene, and polysilicone, or other coatings such as a coating of a beneficial agent or an antimicrobial agent. It shall be understood that the coatings listed above are merely exemplary and should not be considered limiting in any manner.

In addition, the material 300 may be utilized to model surfaces and/or devices such as medical devices which may be in contact with a patient during a medical procedure. For example, stainless steel may be utilized to model a medical device such as a scalpel, scissors, or stent. Further still, the material may comprise materials such as silicone or polyvinyl chloride which may be sectioned from a catheter.

As shown in FIG. 2 the vessel 105 serves two important functions for biofilm/encrustation development. The first function is as a reservoir for the liquid growth medium containing biofilm forming organisms which will form a biofilm on the projections 130. The second function of the vessel is to generate a shear force across the projections. The generated shear force allows for optimal biofilm/encrustation formation on the projections. The biofilm forming organisms may, for example, be protozoa, spores, viruses, bacteria, yeast, or fungi. The fungi may further be filamentous fungi. The shear force developed in the vessels may be generated by a rocking table or a gyrating shaker. The proper device for generating the shear force will be chosen according to which vessel is utilized in the assembly. In the instances where the vessel 105 is being utilized, the use of a gyrating shaker is preferred. The gyrating shaker is preferred because the motions that are produced cause a centrifugal force to be generated in the liquid growth medium. This centrifugal force is necessary because it causes consistent formation of biofilm on the projections or material disposed upon the projections of the lid 90 by causing the liquid growth medium to pass over the projections evenly. An appropriate gyrating shaker may be obtained from New Brunswick Scientific Co. Inc.

Although each embodiment has been described in a preferred embodiment, it is contemplated that either method of providing flow of the liquid growth medium may be utilized for each assembly. It shall be understood that the gyrating shaker is preferably utilized with the vessel 105 because the gyrating shaker generates centrifugal forces in the liquid growth medium, thus causing the liquid growth medium to flow around the projections and/or material disposed within each of the wells. If the rocking table was utilized with the vessel 105, the rocking motion may cause some of the liquid growth medium to contact the un-coated portions of the material disposed within the wells, thereby interfering with the formation of the biofilm on the coated surfaces as described above. Furthermore, because the wells 125 have a generally cylindrical shape, the centrifugal motion is the most efficient motion to use in order to provide laminar flow of the liquid. In addition, the gyrating shaker may be utilized with the alternative embodiment of the present invention in order to provide laminar flow of the liquid growth medium across the plurality of projections and/or material disposed therein, though the biofilm formation may not be uniform across the projection/material as it would be if the rocking table was utilized.

While it is possible to form biofilm/encrustation with only one direction of fluid flow, the vessel must be designed so that the fluid may flow into the vessel in one side and out of the vessel in another side, thereby increasing the costs of the device as well as the complexity. By contrast the constant motion and the turbulence that results from the rocking or shaking, and the design of the vessel (i.e., wells, troughs, recesses, or similar geometries) is simple to achieve, and has been found effective to achieve even biofilm growth.

METHODS OF USE

A test device was prepared to test the performance of various antimicrobial ureteral stent coatings with their ability to prevent microorganism attachment, colonization, biofilm formation and encrustation under Good Laboratory Practice (GLP) conditions.

An artificial urine growth media was prepared according to the following:

| In g/Liter distilled water | | Grams |
|---|---|---|
| 1 | Peptone L37 | 1.0 |
| 2 | Yeast Extract | 0.005 |
| 3 | Lactic Acid | 0.1 |
| 4 | Citric Acid | 0.4 |
| 5 | Sodium Bicarbonate | 2.1 |
| 6 | Urea | 10.0 |
| 7 | Uric Acid | 0.07 |
| 8 | Creatinine | 0.8 |
| 9 | Calcium Chloride.$H_2O$ | 0.37 |
| 10 | Sodium Chloride | 5.2 |
| 11 | Iron II Sulphate.7 $H_2O$ | 0.0012 |
| 12 | Sodium Sulphate.10 $H_2O$ | 0.49 |
| 13 | Magnesium Sulphate.10 $H_2O$ | 3.2 |
| 14 | Potassium dihydrogen phosphate | 0.95 |
| 15 | Di-potassium hydrogen phosphate | 1.2 |
| 16 | Ammonium Chloride | 1.3 |
| 17 | Distilled $H_2O$ | To 1 Liter |

A clinical strain of *P. mirabilis* was used in the study. The strain was preserved by freezing (in preservative at −70° C. to −80° C.) after a minimum number of transfers. Prior to inoculation in the test apparatus, the isolate was incubated for 18–24 hours at 37° C. in Tryptic Soy broth under gentile shaking, washed two times in PBS, pH 7.1 then resuspended in $DH_2O$ (37° C.) to a titer of approximately $10^9$ cells/mL. The *P. mirabilis* was diluted 1:20 prior to inoculating microtitre wells containing artificial urine to achieve approximately $10^7$ cells/well.

Both "positive" (with antimicrobial coating) and "negative" (uncoated stents) ureteral stents were prepared for study, controls and three test stents were submitted for the test protocol using the testing device 90 described above. As shown in FIG. 3, the stents (sectioned in 3-cm pieces) were secured to the lid of the test device, wherein each end of the stent portions were disposed on adjacent pins thereby forming a general unshaped portion to be received within the well 125 of the testing device when the lid 120 is placed thereupon.

Three stent portions were tested per coating type (including positive and negative controls) for each sampling period. The positive control samples were tested in a different device from the negative samples. After the stents were prepared according to the procedure described above, the testing device and the stents were ethylene oxide sterilized and exposed to the *P. mirabilis* and artificial urine sample as prepared above. The artificial urine media was replaced with fresh sterile media/bacteria every twenty-four hours.

Each of the tests were run in triplicate for a four week period. The following table provides the distribution of the test.

| TEST | Stents | Encrustation | Micro | SEM |
|---|---|---|---|---|
| pH 5 - no bacteria | +control, −control, 3 test | 4 Wk | | 4 Wk |
| pH 5 - bacteria | +control, −control, 3 test | 4 Wk | 4 Wk | 4 Wk |
| pH 7 - no bacteria | +control, −control, 3 test | 4 Wk | | 4 Wk |
| pH 7 - bacteria | +control, −control, 3 test | 4 Wk | 4 Wk | 4 Wk |
| pH 8.5 - no bacteria | +control, −control, 3 test | 4 Wk | | 4 Wk |
| pH 8.5 - bacteria | +control, −control, 3 test | 4 Wk | 4 Wk | 4 Wk |
| Low Oxalate - no bacteria | +control, −control, 3 test | 4 Wk | | 4 Wk |
| Low Oxalate - bacteria | +control, −control, 3 test | 4 Wk | 4 Wk | 4 Wk |
| High Oxalate - no bacteria | +control, −control, 3 test | 4 Wk | | 4 Wk |
| High Oxalate - bacteria | +control, −control, 3 test | 4 Wk | 4 Wk | 4 Wk |

Figure 5:
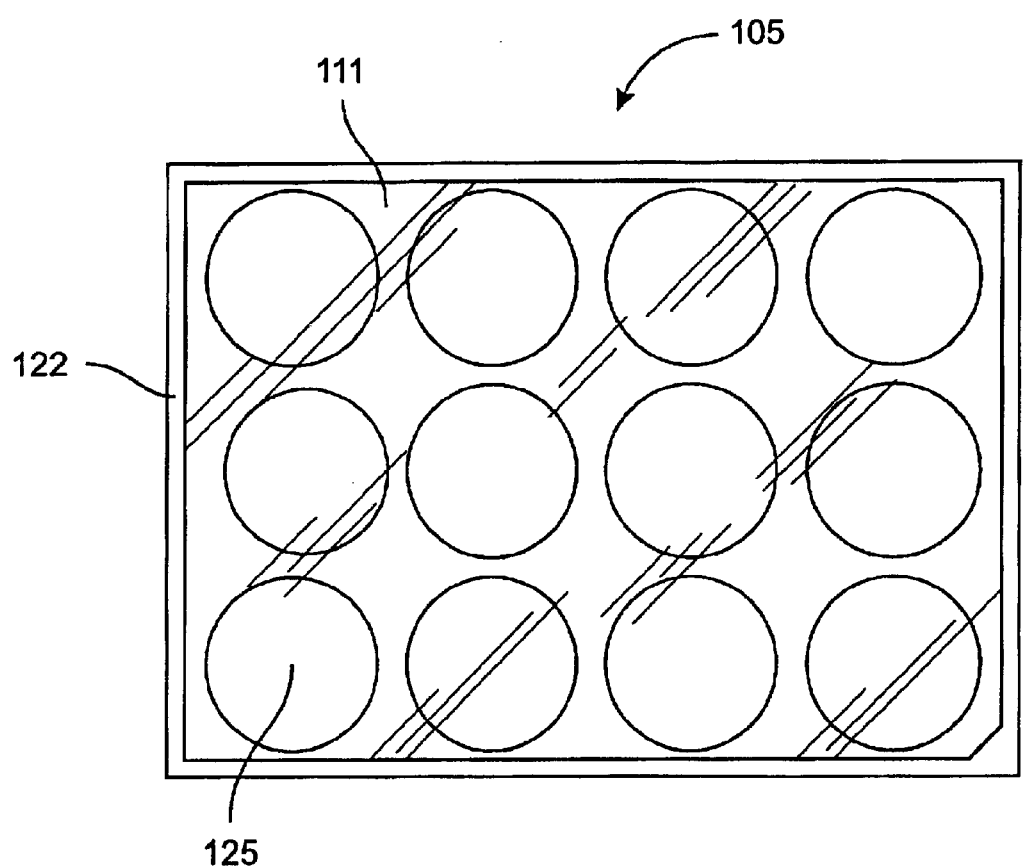
FIG. 5 is a top view of an exemplary embodiment of the vessel in accordance with one embodiment of the present invention.
Figure 6:
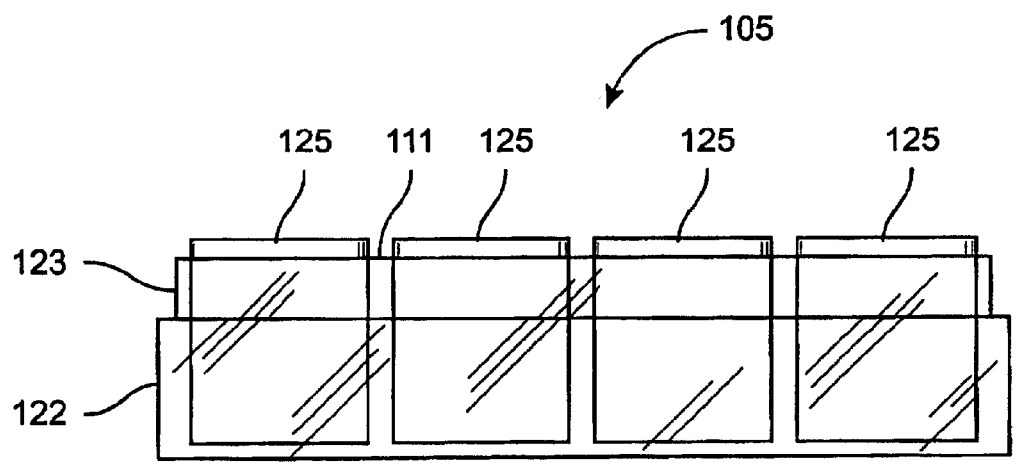
FIG. 6 is a side view of an exemplary embodiment of the vessel in accordance with one embodiment of the present invention.

At the four week point, the stents (3 of each material) were placed in 5 mL sterile deionized water for rinsing to remove reversibly bound cells from the surface of the stents, each stent underwent two ten second rinses. After rinsing, the stents were placed into the wells of a twelve well microtitre plate 105, as shown in FIGS. 5 and 6, containing 5 mL of sterile water. The stents were then sonicated for 5 minutes using a low frequency Bransonic-type sonicator to remove adherent organisms. The bacterial colonization was determined by dilution plate counts on nutrient agar. As inactive reagents cannot be used, the presence of biocide released from the stent during the bacterial recovery phase was compensated by serial ten-fold dilutions.

At four weeks, stents (3 of each material) were immersed in 5 ML of 4.0% (v/v) nitric acid (metal oxide semiconductor grade in double-deionized water) in universal containers. The encrustations were disrupted by sonicating the stents for five minutes. The crystalline suspensions were left for twenty-four hours to dissolve before the solutions were analyzed for calcium and magnesium content. The solutions were analyzed utilizing atomic absorption spectroscopy (AAS/ICP) for inorganic constituents. Further still, scanning electron microscopy was performed on one of the stents of each material and test condition four weeks after the study was initiated.

RESULTS

Effect of pH on Encrustation

It was determined that there was no appreciable difference between the colonization of Proteus among the different stent materials. At pH 5.0, encrustation was similar between stents colonized with bacteria and sterile stents. Furthermore, these stents had significantly less encrustation than the stents placed in urine at pH 7 and pH 8.5. At higher pH's, there was also no difference in the encrustation among the stents with bacteria and without bacteria. There was significantly more encrustation in the stents exposed to bacteria. The low encrustations at high pH was associated with precipitation of urinary salts at high pH due to the lesser amounts of salts to encrust the stents.

Effect of Oxalate Concentration on Encrustation

It was determined that the was no appreciable difference between the stents exposed to high and low oxalate concentrations. Oxalate concentration did not influence encrustation.

The results of each of these tests can be seen below with reference to Tables 1 and 2 as follows:

TABLE 1

The effect of pH on encrustation of stents exposed to proteus bacteria or only to sterile urine.

| stent Id | CFU/ML SAMPLE | | | CALCIUM ON STENT (MG/STENT) | |
|---|---|---|---|---|---|
| | A | B | C | With Proteus | Sterile |
| pH 5.0 | | | | | |
| 1 | 7.0 E6 | 1.2 E7 | 5.0 E6 | 41.9 | 41.1 |
| 2 | 8.0 E6 | 3.5 E6 | 4.5 E6 | 33.7 | 32.4 |
| 13 | 2.5 E6 | 1.1 E7 | 1.5 E6 | 35.3 | 34.9 |
| 18 | 6.0 E6 | 3.0 E6 | 3.0 E6 | 30.4 | 31.2 |
| 20 | 1.1 E7 | 4.5 E6 | | 33.7 | 37.4 |
| pH7.0 | | | | | |
| 1 | 7.0 E7 | 3.0 E7 | | 363.7 | 211.9 |
| 2 | 3.5 E6 | 3.5 E6 | | 325.7 | 243.2 |
| 13 | 5.0 E6 | N.S. | | 380.2 | 211.9 |
| 18 | 3.5 E5 | 4.5 E5 | | 332.3 | 215.6 |
| 20 | 3.5 E6 | 3.0 E6 | | 371.9 | 250.2 |
| pH 8.5 | | | | | |
| 1 | 7.5 E6 | 5.0 E6 | | 157.4 | 88.1 |
| 2 | 5.0 E6 | 2.0 E6 | | 117.8 | 91.4 |
| 13 | 6.5 E5 | 6.0 E5 | | 145.9 | 99.3 |
| 18 | 1.4 E6 | 1.2 E6 | | 111.2 | 85.6 |
| 20 | 4.0 E4 | 9.5 E4 | | 134.3 | 95.5 |

TABLE 2

The effect of oxalate on encrustation of stents exposed to proteus bacteria or only to sterile urine.

| Stent Id | CFU/ML SAMPLE | | | CALCIUM ON STENT (MG/STENT) | |
|---|---|---|---|---|---|
| | A | B | C | With Proteus | Sterile |
| LOW OXALATE | | | | | |
| 1 | 1.3 E7 | 6.5 E6 | 8.0 E6 | 279.5 | 226.7 |
| 2 | 4.0 E5 | 2.0 E5 | 1.0 E6 | 292.7 | 221.8 |
| 13 | 1.5 E6 | 6.0 E5 | 7.5 E5 | 271.3 | 219.3 |
| 18 | 1.2 E6 | 2.0 E6 | 4.5 E5 | 287.8 | 198.3 |
| 20 | 2.0 E6 | 9.5 E5 | 3.0 E5 | 330.7 | 219.3 |
| HIGH OXALATE | | | | | |
| 1 | 2.5 E7 | 2.5 E7 | 3.5 E7 | 391.7 | 243.2 |
| 2 | 2.5 E6 | 7.0 E5 | 3.0 E6 | 360.4 | 216.8 |
| 13 | 3.0 E6 | 5.0 E5 | 5.0 E6 | 385.1 | 225.1 |
| 18 | 3.5 E6 | 2.5 E4 | 4.0 E6 | 388.4 | 219.3 |
| 20 | 1.1 E6 | 1.1 E6 | 5.0 E6 | 376.9 | 213.1 |

Scanning Electron Micrographs

Bacteria were observed within the crystal matrix of the urinary catheters. Bacteria were also observed to be present on the surfaces of the stent. The observed bacteria were encased in an exopolysaccharide glycocalyx. There was no difference between the appearance of bacteria or crystal formation among the stent materials.

Thus it can be seen that the testing device in accordance with the present invention allows a variety of materials to be tested for the formation of biofilms and encrustation thereon. In addition, the present invention provides a device that enables a plurality of antimicrobial coatings to be separately investigated.

It shall be understood that the methods and apparatus described herein shall not be considered limiting. It shall be understood to one skilled in the art that modifications could be made to the invention as described herein without departing from the essence of the invention that is intended to be covered by the scope of the claims that follow.

What is claimed is:

1. A method for testing the performance of surface coatings and the ability to prevent the formation of an encrustation deposit on a material, said method comprising:
   providing a plurality of material retaining sites;
   providing said material retaining sites with a material, wherein said material models a surface to be involved in an encrustation deposit;
   providing a liquid medium, arranged to cover at least a portion of said material; and
   incubating said encrustation deposit on said material retaining sites in the presence of said liquid medium.

2. The method of claim 1 wherein said encrustation deposit is at least one of calcium, salt, mineral or thrombus.

3. The method of claim 1, further comprising a step of coating said material.

4. The method of claim 3, wherein said coating is chosen from the group consisting of aluminum, stainless steel, silver, copper, hydroxyapatite, silicon, latex, urethane, PVC, ceramic, steel, gold, titanium, polyethylene, antimicrobial, and polysilicone.

5. The method of claim 1, further comprising a step of agitating said liquid medium, such that said liquid medium flows across said material.

6. The method of claim 3, wherein said coating is disposed upon said material retaining sites.

7. The method of claim 1, wherein said material retaining sites are in the form of a projection.

8. The method of claim 1, wherein said material is a portion of a medical device.

9. The method of claim 8, wherein said medical device is a catheter affixed to said material retaining sites.

10. The method of claim 8, wherein said medical device is a stent affixed to said material retaining sites.

11. The method of claim 5, wherein said step of agitating said liquid growth medium is provided by a gyrating shaker.

12. The method of claim 1, further comprising a step of disrupting said encrustation deposit by sonicating said material retaining site.

13. The method of claim 1, further comprising a step of assaying said encrustation deposit.

14. The method of claim 1, further comprising a step of deionizing said material retaining sites.

15. The method of claim 1, wherein said liquid medium includes at least one microorganism.

16. The method of claim 15, further comprising a step of exposing said microorganism to a biocide.

17. The method of claim 15, wherein said microorganism is chosen from the group consisting of protozoa, spores, viruses, bacteria, yeast or fungi.

18. The method according to claim 15, further comprising incubating said microorganism on said material retaining sites in the presence of said liquid medium.

19. A method for testing the effect of materials and surface coatings on the formation of an encrustation deposit in a controlled environment, said method including:
   providing a plurality of encrustation adherent sites;
   coating said encrustation adherent sites with a material which acts as a model for a surface to be involved in an encrustation formation;
   providing a liquid medium arranged to flow across said encrustation adherent sites;

agitating said liquid medium;

growing an encrustation deposit on said encrustation adherent sites; and measuring said encrustation deposit on the material.

20. The method of claim 19, wherein the encrustation is at least one of calcium, salt, mineral or thrombus.

21. The method of claim 19, wherein said coating is chosen from the group consisting of, aluminum, stainless steel, silver, copper, hydroxypatite, silicon, latex, urethane, PVC, ceramic, steel, gold, titanium, polyethylene, antimicrobial, and polysilicone.

22. The method of claim 21, further comprising a step of adhering said coating to said encrustation adherent sites with an adhesive.

23. The method of claim 19, further comprising a step of disrupting said encrustation deposit by sonicating said material retaining site.

24. The method of claim 19, wherein said liquid medium includes at least one microorganism.

25. The method of claim 24, wherein said microorganism is chosen from the group consisting of protozoa, spores, viruses, bacteria, yeast, or fungi.

26. The method according to claim 19, further comprising incubating said microorganism on said material retaining sites in the presence of said liquid medium.

27. A method for testing a material for the formation of encrustations, the method comprising:

disposing a material on a plurality of material retaining sites;

providing a liquid medium, wherein said liquid medium comprises at least one microorganism, arranged to cover at least a portion of said material; and incubating said material retaining sites in the presence of said liquid medium to promote encrustation formation.

28. The method of claim 27, wherein the encrustation is at least one of calcium, salt, mineral or thrombus.

29. The method of claim 27, further comprising a step of flowing said liquid medium across said material.

30. The method of claim 27, further comprising a step of coating said material.

31. The method of claim 30, wherein said coating is an anti-microbial coating.

32. The method of claim 30, wherein said coating is a beneficial agent.

33. The method of claim 27, further comprising a step of sonicating said encrustations to disrupt said encrustations from said material.

34. The method of claim 30, further comprising a step of analyzing said encrustations to compare said coating with its ability to prevent said formation of encrustations.

35. The method of claim 30, wherein said coating is chosen from the group consisting of aluminum, stainless steel, silver, copper, hydroxyapatite, silicon, latex, urethane, poly vinyl chloride (PVC), ceramic, steel, gold, titanium, polyethylene, antimicrobial, and polysilicone.

36. The method of claim 27, further comprising a step of agitating said liquid medium, such that said liquid medium flows across said material.

37. The method of claim 27, wherein said coating models a medical device.

38. The method of claim 27, wherein said microorganism is chosen from the group consisting of protozoa, spores, viruses, bacteria, yeast or fungi.

39. The method according to claim 27, further comprising incubating said at least one microorganism on said material retaining sites in the presence of said liquid medium.

\* \* \* \* \*